US008273033B2

(12) United States Patent
Orr et al.

(10) Patent No.: US 8,273,033 B2
(45) Date of Patent: Sep. 25, 2012

(54) TEMPERATURE COMPENSATION OF A RESPIRATORY GAS SENSOR

(75) Inventors: Joesph A. Orr, Park City, UT (US);
Paul B. Gunneson, Cheshire, CT (US);
Anthony T. Pierry, Plantsville, CT (US)

(73) Assignee: RIC Investments, LLC, Wilmington, DE (US)

( * ) Notice: Subject to any disclaimer, the term of this patent is extended or adjusted under 35 U.S.C. 154(b) by 1315 days.

(21) Appl. No.: 11/958,872

(22) Filed: Dec. 18, 2007

(65) Prior Publication Data
US 2008/0161711 A1 Jul. 3, 2008

Related U.S. Application Data

(60) Provisional application No. 60/876,799, filed on Dec. 21, 2006.

(51) Int. Cl.
*A61B 5/00* (2006.01)

(52) U.S. Cl. ..... 600/532; 600/529; 600/538; 422/82.08; 422/84; 436/136; 73/23.3

(58) Field of Classification Search .................. 600/529, 600/532, 538, 531; 73/23.27, 23.29
See application file for complete search history.

(56) References Cited

U.S. PATENT DOCUMENTS

| 4,859,859 A * | 8/1989 | Knodle et al. ............ 250/504 R |
| 5,789,660 A | 8/1998 | Kofoed et al. |
| 6,001,064 A * | 12/1999 | Weckstrom .................. 600/532 |
| 6,174,289 B1 * | 1/2001 | Binder ......................... 600/532 |
| 6,312,389 B1 | 11/2001 | Kofoed et al. |
| 6,325,978 B1 | 12/2001 | Labuda et al. |
| 6,520,180 B1 * | 2/2003 | Sahmkow et al. ....... 128/204.21 |
| 6,616,896 B2 | 9/2003 | Labuda et al. |
| 6,632,402 B2 | 10/2003 | Blazewicz et al. |
| 6,815,211 B1 | 11/2004 | Blazewicz et al. |
| 6,888,101 B2 | 5/2005 | Davis |
| 2002/0029003 A1 | 3/2002 | Mace et al. |
| 2004/0013570 A1 * | 1/2004 | Labuda et al. ............. 422/82.08 |
| 2005/0145796 A1 | 7/2005 | Davis |
| 2006/0009707 A1 | 1/2006 | Daniels et al. |
| 2006/0014078 A1 | 1/2006 | Swoyer et al. |
| 2007/0107728 A1 * | 5/2007 | Ricciardelli et al. ..... 128/204.21 |

OTHER PUBLICATIONS

U.S. Appl. No. 11/948,080, filed Nov. 30, 2007, Orr et al.

* cited by examiner

*Primary Examiner* — Patricia Mallari
*Assistant Examiner* — Michael Catina

(57) ABSTRACT

A mainstream gas monitoring system and method that includes a mainstream airway adapter, and a gas sensing assembly associated with the mainstream airway adapter to measure an analyte of a gas flow through the adapter. A gas sensing portion outputs a signal indicative of the analyte in a gas flow in the mainstream airway adapter. A processing portion receives the signal from the gas sensing portion and determines an amount of the analyte in the gas flow based on the signal from the gas sensing portion. The gas sensing portion is subject to temperature variations associated with variations in flow rate and direction of respiratory gases. Methods are described that utilize the measurement of instantaneous respiratory flow rate combined with estimates of gas temperature and composition to estimate the sensor cooling effects from which a flow based time varying compensation factor is derived.

30 Claims, 12 Drawing Sheets

TEMPERATURE COMPENSATION OF A RESPIRATORY GAS SENSOR

CROSS-REFERENCE TO RELATED APPLICATIONS

This application claims priority under 35 U.S.C. §119(e) from provisional U.S. patent application No. 60/876,799 filed Dec. 21, 2006 the contents of which are incorporated herein by reference.

BACKGROUND OF THE INVENTION

1. Field of the Invention

The present invention pertains to a system and method for compensating for effects of gas temperature fluctuations on respiratory gas sensing devices in airway flow measurement systems.

2. Description of the Related Art

It is well known to monitor the oxygen consumption or oxygen uptake of an individual for purposes of monitoring the physiologic condition of that person. The phrases "oxygen update" and "oxygen consumption" are used synonymously, and are both represented by the expression "$V_{O_2}$," or, for simplicity "$VO_2$". Oxygen consumption is a measure of the amount of oxygen that the body uses in a given period of time, such as one minute. It is typically expressed as milliliters of oxygen used per kilogram of body weight per minute (ml/kg/min). Measuring the rate of oxygen consumption is valuable, for example, in anesthesia and intensive care situations because it provides an indication of the sufficiency of a patient's cardiac and pulmonary function. $VO_2$ can also be used to monitor the fitness of an individual or athlete.

$VO_2$ is conventionally calculated as the difference between the volume of oxygen inspired and the volume of oxygen expired. The standard or direct calculation of $VO_2$ is given by the following equation:

$$VO_2 = Vi * Fi_{O2} - Ve * \overline{Fe}_{O2}, \tag{1}$$

where: "$VO_2$" is oxygen consumption, "Vi" is inspired volume, "$Fi_{O2}$" is the inspired oxygen concentration, "Ve" is the expired volume, and "$\overline{Fe}_{O2}$" is the mixed expired oxygen concentration.

An alternative method of calculating $VO_2$ uses only the expired breath volume, Ve. In this scenario, the inspired breath volume Vi is calculated (rather than measured) based on the assumption that the nitrogen volume is the same for both inspired and expired gas, which is usually true because nitrogen is not consumed or produced by the body. This is referred to as the nitrogen balance. The calculation of Vi, rather than measuring it, also assumes that the effect of temperature and humidity are the same for both inspired and expired gas volumes.

This modification of equation (1), which uses a calculation of Vi based on the nitrogen balance noted above, is known as the Haldane transform. According to this technique, Vi is calculated as follows:

$$Vi = Ve * \overline{Fe}_{N2}/Fi_{N2}, \tag{2}$$

where "$\overline{Fe}_{N2}$" is the concentration of expired nitrogen, and "$Fi_{N2}$" is the concentration of inspired nitrogen. Based on this, the Haldane transform becomes:

$$Vi = Ve * (1 - \overline{Fe}_{CO2} - \overline{Fe}_{O2})/(1 - Fi_{CO2} - Fi_{O2}), \tag{3}$$

and the oxygen consumption calculation becomes:

$$VO_2 = Ve * [Fi_{O2} * ((1 - \overline{Fe}_{CO2} - \overline{Fe}_{O2})/(1 - Fi_{CO2} - Fi_{O2})) - \overline{Fe}_{O2}], \tag{4}$$

where $\overline{Fe}_{CO2}$ is the expired carbon dioxide concentration, and $Fi_{CO2}$ is the inspired carbon dioxide concentration.

Calculating $VO_2$ using the Haldane transform has the advantage that the effects of errors in volume measurements that are not "common mode" are eliminated, because only the expired volume measurement is used. Common mode errors are errors that effect both the Vi and Ve measurements, such as a calibration error in a flow sensor. Assuming, of course, the same sensor is used to measure Ve and Vi and the sensor performs consistently under variable conditions in its operating environment.

Mainstream sensors used to measure respiratory gas constituents can be subject to interference due to cyclical cooling effects of the flow of large volumes of gas past the sensor. Certain sensor technologies rely on one or more temperature controlled sensing elements placed within or near the gas stream. For example, certain oxygen sensitive elements located within the respiratory gas stream rely on the principle of fluorescence quenching to measure oxygen content in a flow, wherein the oxygen sensitive element is maintained at a constant temperature to obtain accurate measurements.

Because such an oxygen sensitive element must be in direct contact with the flowing respiratory gas, it is impractical to entirely eliminate or completely correct for temperature fluctuations resulting from respiratory flow changes. More generally, the operation of temperature controlled sensing elements can be affected by gas flows that have variable flow rates and that change direction, because temperature control systems may be unable to track flow-induced temperature changes with sufficient speed to avoid an adverse impact on the sensor operation.

SUMMARY OF THE INVENTION

Accordingly, it is an object of the present invention to provide a gas monitoring system that overcomes the shortcomings of conventional gas monitoring systems. In particular, certain embodiments of the present invention resolve the problem of respiratory gas cooling effects on certain types of mainstream gas sensing devices used in spirometry, gas monitoring, and other applications. When such a sensor is used in conjunction with a flow monitor, a pressure monitor, or both in order to estimate oxygen consumption and related metabolic parameters, the present invention provides methods for correcting errors in the oxygen measurement caused by these temperature fluctuations. Methods provided in accordance with aspects of the invention utilize the measurement of instantaneous respiratory flow rate combined with estimates of gas temperature and composition to estimate the sensor cooling effects from which a flow based time varying compensation factor is derived.

In accordance with one embodiment of the invention, there is provided a system for measuring an amount of a gas component within a gas flow that includes a gas sensor constructed and arranged to measure an amount of a component of gas within a flow of gas. The gas sensor has a sensing element that is constructed and arranged to be in contact with the flow of gas. The sensing element has an output that is sensitive to temperature fluctuations thereof. A flow sensor, pressure sensor, or both are constructed and arranged to measure flow or pressure of the flow of gas. A processor receives first signals as a function of the amount of the component of gas measured by the gas sensor, and second signals as a function of the flow measured by the flow sensor or pressure measured by the pressure sensor. The processor adjusts the measurement of the amount of the component of gas measured by the gas sensor based upon the measured flow or pressure of the gas flow.

In accordance with another embodiment of the present invention, there is provided a system for measuring an amount of oxygen in a gas flow. The system includes a conduit through which gas flows, and an oxygen sensor having a sensing element exposed to the gas flow within the conduit. The oxygen sensor senses an amount of oxygen in the gas flow. The system also includes a sensor constructed and arranged to measure a characteristic associated with the gas flow in the conduit, such as a rate of flow or a pressure. A processor that receives signals based on the amount of oxygen sensed by the oxygen sensor and based on the measured characteristic. The processor adjusts the oxygen measured by the oxygen sensor based on the characteristic measured by the sensor.

In accordance with another embodiment of the present invention, there is provided a method of measuring an amount of oxygen in a flow of gas, measuring a characteristic associated with the gas flow (such as rate of flow or pressure), and adjusting the measurement of the amount of oxygen in the flow of gas based upon the characteristic of the gas flow.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
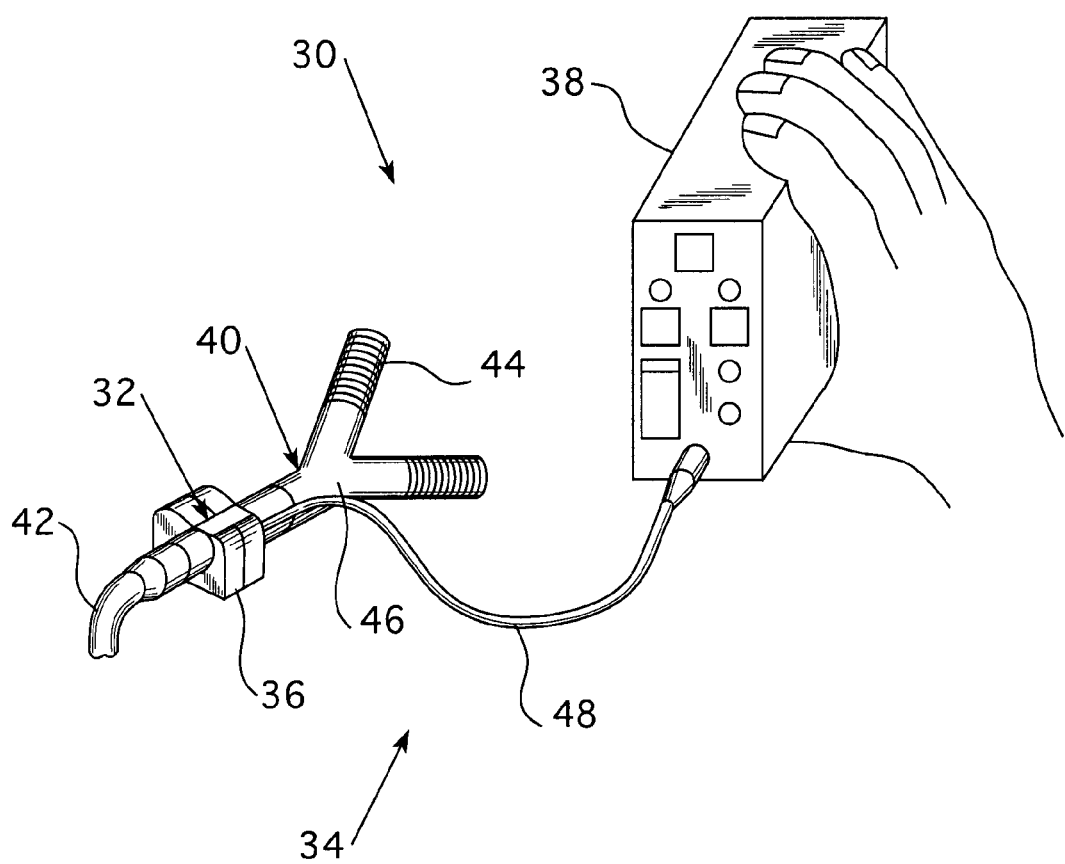
FIG. 1 is a perspective view of a first embodiment of a gas sensing system according to the principles of the present invention.

FIG. 1 schematically illustrates an exemplary embodiment of a mainstream gas monitoring system 30 that employs the principles of the present invention. Gas monitoring system 30 includes an airway adapter 32 for use in a respiratory circuit 40, and a gas sensing assembly, generally indicated at 34. Respiratory circuit 40 is used to communicate a flow of gas to a patient. For example, a first end 42 of respiratory circuit 40 is connected with a patient interface appliance configured to communicate with an airway of a patient. Examples of patient interface appliances that are suitable for use with respiratory circuit 40 include, but are not limited to: an endotracheal tube, a nasal cannula, a tracheotomy tube, a mask, or any other device or apparatus that communicates a flow of gas with an airway of a user.

A second end 44 of respiratory circuit 40 is configured to communicate with a gas source. For instance, the gas source may include ambient atmosphere, a supply of pressurized gas, a pressure support device, a ventilator, or other sources of gas. In the illustrated embodiment, second end 44 comprises a Y-connector 46, which is typically found in a ventilator circuit, connected to the second end of the airway adapter. One leg of the Y-connector corresponds to the inspiratory limb, which delivers gas from a ventilator (not shown) to the patient, and the other leg of the Y-connector corresponds to the expiratory limb, which delivers gas from the patient. Typically, the gas is delivered by the expiratory limb back to the ventilator, which is the gas source in this embodiment. In a single limb system (not shown), the second end comprises a single conduit that communicates a flow of gas between the patient and the gas source, which is often a pressure support system, such as a CPAP, bi-level, or auto-titrating pressure support device.

Figure 2:
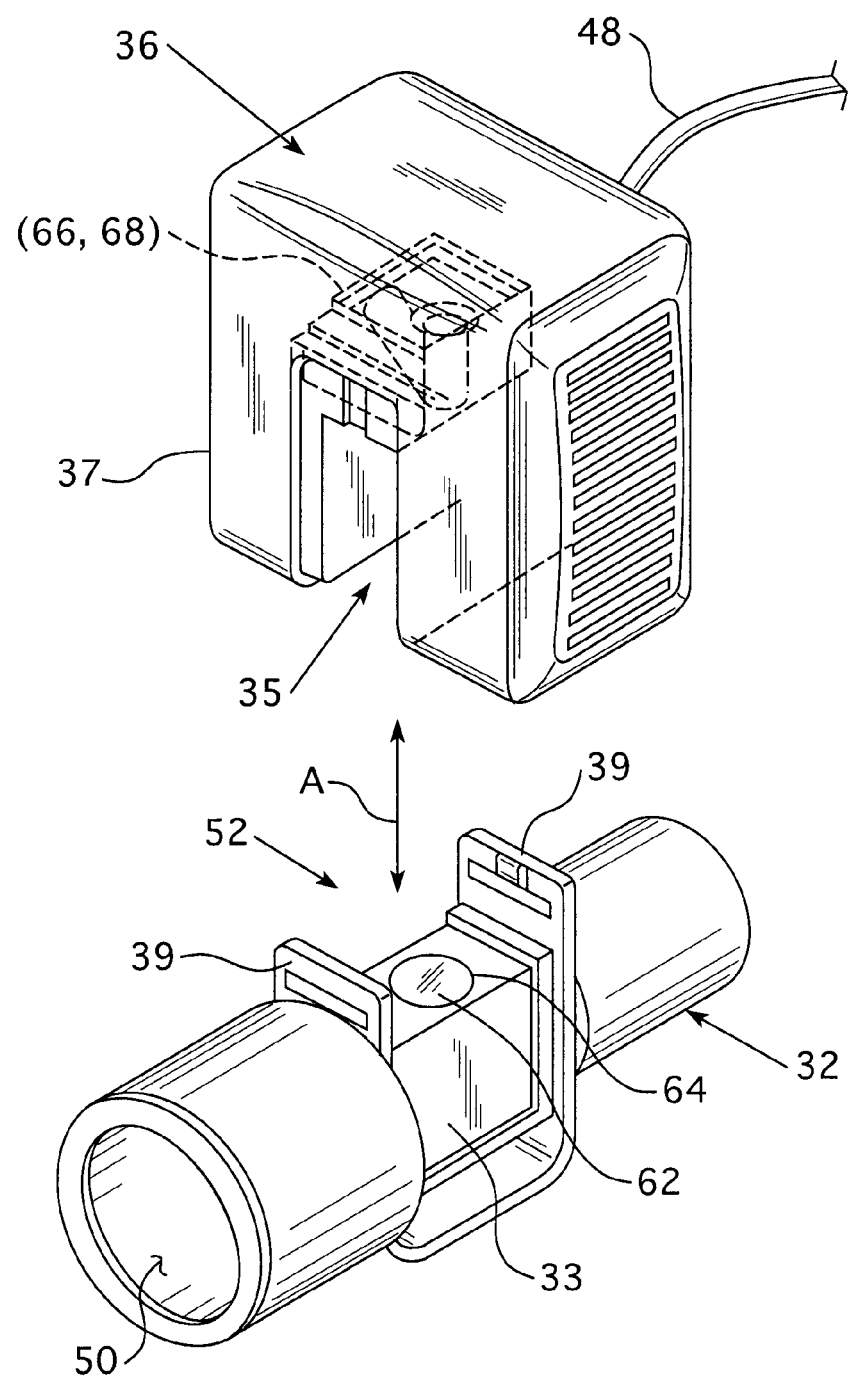
FIG. 2 is a perspective view of an airway adapter and gas sensor in the gas sensing system of FIG. 1.
Figure 3:
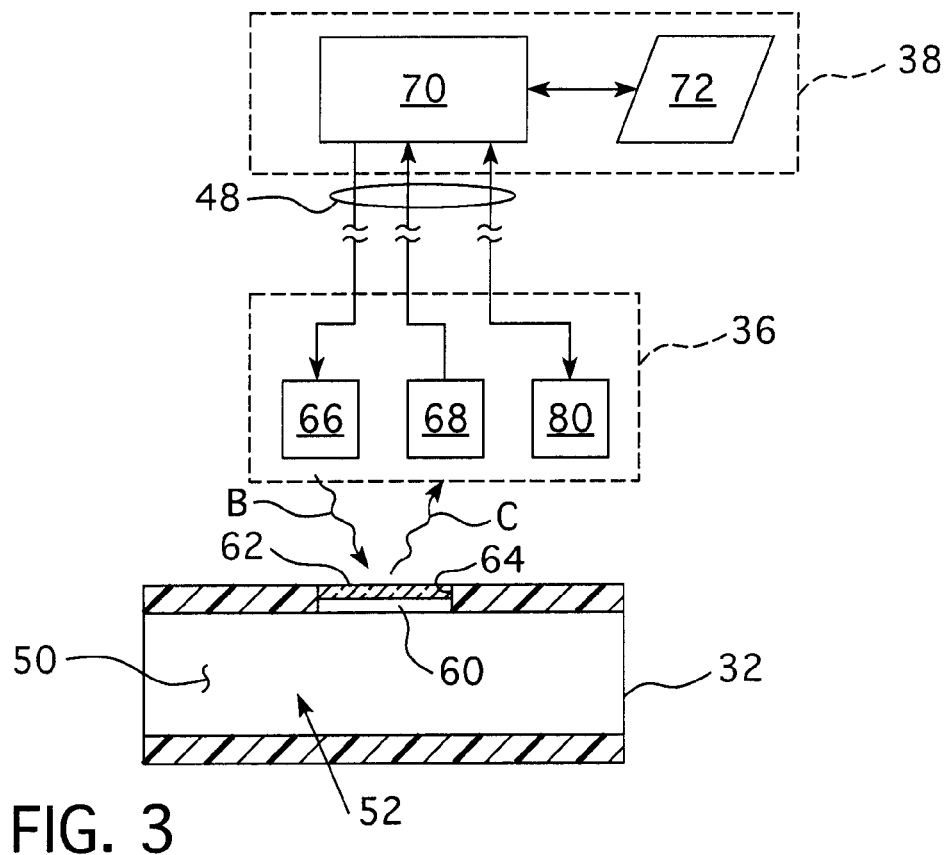
FIG. 3 is a schematic view of the components of the gas sensing system of FIG. 1.

As perhaps best shown in FIGS. 2 and 3, airway adapter 32 provides a flow path 50 in-line with respiratory circuit 40 through which gas passes to and from the patient. Airway adapter 32 also provides a gas monitoring portion or sample site, generally indicated at 52, at which the constituents of the gas passing through the airway adapter 32 are monitored or measured. Examples of airway adapter suitable for use in the present invention are described in U.S. Pat. No. 5,789,660 ("the '660 patent") and U.S. Pat. No. 6,312,389 ("the '389 patent"), and in U.S. patent application Ser. No. 09/841,451 ("the '451 application," published as publication no. 2002/0029003), the contents of each of which are incorporated herein by reference in their entirety.

In the embodiment illustrated in FIGS. 1-3, gas sensing assembly 34 includes a gas sensing portion 36 and a processing portion 38. In this illustrated exemplary embodiment, gas sensing portion 36 is removably coupled to airway adapter 32, as indicated by arrow A, and includes the components that are used to detect the gas constituent or constituents, also referred to as analyte, being monitored. It should be appreciated that a variety of mechanisms may be implemented to removably couple gas sensing portion 36 to airway adapter 32. In an exemplary embodiment shown in FIG. 2, a seating area 33 is provided on an outer surface of airway adapter 32 that is adapted to securely receive a housing 37 of gas sensor portion 36. Housing 37 is generally "U" shaped to fit onto seating area 33 with a channel 35 that receives the generally matching shape of the seating area of the airway adapter. Flanges 39 can be provided on the airway adapter to align and attach the housing to the airway adapter. U.S. Pat. No. 6,616,896 ("the '896 patent") and U.S. Pat. No. 6,632,402 ("the '402 patent"), the contents of each of which are incorporated hereby by reference, describe techniques for coupling gas sensing portion 36 to airway adapter 32. The present invention also contemplates permanently connecting gas sensing portion 36 to airway adapter 32 so that the functionality of each component is effectively combined into a common element.

A communication link 48 allows data, power, and any other signals, commands, etc. to be communicated between gas sensing portion 36 and processing portion 38. Although a hard wired communication link 48 is shown in FIGS. 1-3, it is to be understood that the present invention contemplates that the communication link can be a wireless link, using any form of wireless communication or communication protocol. Of course, if a wireless link is provided, a power supply, such as battery, must be included in gas sensing portion 36 or a power must be provided in some other manner to the gas sensing portion.

Gas sensing assembly 34 detects the concentration of one or more gases (analytes) in the flow of gas through the sample cell. In an exemplary embodiment illustrated in FIGS. 1-3, gas sensing assembly 34 is configured to employ luminescence quenching techniques to measure the partial pressure or amount of oxygen or other gases that flow through airway adapter 32. This oxygen measurement is used, for example, to determine the value for $Fi_{O2}$ and $\overline{Fe}_{O2}$.

Luminescence quenching is a technique that has been used to measure oxygen concentrations in gases. In using luminescence quenching to measure oxygen concentrations, a luminescable material 60 (see FIG. 3) is excited to luminescence by delivering an excitation energy, as indicated by arrow B, to the luminescable material. Upon being exited to luminescence, the luminescable material will emit energy, as indicated by arrow C. However, when the luminescing material is exposed to a gas mixture including oxygen, the luminescence is quenched, depending upon the amount (i.e., concentration or fraction) of oxygen to which the luminescable material is exposed, or the amount of oxygen in the gas mixture. Accordingly, the rate of decrease in the amount of luminescence, or quenching of luminescence, of the luminescable material (i.e., the amount of light emitted by the luminescable material) corresponds to the amount of oxygen in the gas mixture. Thus, the energy emitted by the luminescable material can be used to determine the concentration of the gas passing through the airway adapter. U.S. Pat. Nos. 6,325,978; 6,632, 402; 6,616,896; and 6,815,211, the contents of each of which are incorporated herein by reference, all disclose an example of an oxygen sensor that uses luminescence quenching to determine the concentration of a gas, such as oxygen, in the gas flowing through a sample cell.

As shown in FIGS. 1-3, a quantity of luminescable material 60 is situated such that it is exposed to the gas flowing in flow path 50 through airway adapter 32. The present invention also contemplates providing a combination of luminescable materials in communication with the gas flowing through the airway adapter. Porphyrins are an example of a material that may be used as luminescable material 60. Porphyrins are stable organic ring structures that often include a metal atom. When the metal atom is platinum or palladium, the phosphorescence decay time ranges from about 10 µs to about 1,000 µs. Porphyrins are also sensitive to molecular oxygen. When porphyrins are used as luminescable material 60, it is preferred that the porphyrins retain substantially all of their photo-excitability with repeated use. Stated another way, it is preferred that the porphyrins be "photostable". Fluorescent porphyrins, such as meso-tetraphenyl porphines, are particularly photostable. The various types of porphyrins that may be used as luminescable material 60 to facilitate oxygen detection include, without limitation, platinum meso-tetra(pentafluoro)phenyl porphine, platinum meso-tetraphenyl porphine, palladium meso-tetra(pentafluoro)phenyl porphine, and palladium meso-tetraphenyl porphine. Of course, other types of luminescable materials that are known to be quenched upon being exposed to oxygen, carbon dioxide, or another analyzed substance (e.g., gas, liquid, or vapor) may also be used in airway adapters incorporating teachings of the present invention.

In the illustrated embodiment, luminescable material 60 is provided on airway adapter 32, and a window 62 is provided in an opening 64 in the body of the airway adapter to allow excitation energy B to be transmitted to the luminescable material. Window 62 preferably has a high transmittance for wavelengths of excitation radiation, which excite luminescable material 60, as well as for wavelengths of radiation C emitted from luminescable material. For example, window 62 may be formed of sapphire, one or more polymers (e.g., polyethelyne, etc.), a glass, and/or other substantially transparent materials.

In an exemplary embodiment, luminescable material 60 is carried by a membrane or matrix, which is disposed on or comprises an integral part of a surface or wall of the airway adapter defining gas flow path 50. The present invention also contemplates that the luminescable material and associated components, such as a membrane, need not be directly coupled to the airway adapter, but can be selectively coupled so that the luminescable material can be replaced without having to remove or replace the entire airway adapter.

An emitter 66 is provided in gas sensing portion 36 to emit excitation energy B to luminescable material 60. In an exemplary embodiment of the present invention, the energy emitted by emitter 66 includes electromagnetic radiation with a wavelength that causes luminescable medium 60 to luminensce. Emitter 66 may include one or more Organic Light Emitting Diodes ("OLEDs"), lasers (e.g., diode lasers or other laser sources), Light Emitting Diodes ("LEDs"), Hot Cathode Fluorescent Lamps ("HCFLs"), Cold Cathode Fluorescent Lamps ("CCFLs"), incandescent lamps, halogen bulbs, received ambient light, and/or other electromagnetic radiation sources.

In one exemplary implementation, emitter 66 includes one or more green and/or blue LEDs. These LEDs typically have high intensity in the luminescable composition absorption region of luminescable medium 60 and output smaller amounts of radiation at other wavelengths (e.g., red and/or infrared). This minimizes stray interfering light and photo-degradation of the sensor. While, the present invention is by no means limited to the use of LEDs, other advantages of implementing LEDs as emitter 66 include their light weight, compactness, low power consumption, low voltage requirements, low heat production, reliability, ruggedness, relatively low cost, and stability. Also they can be switched on and off very quickly, reliably, and reproducibly.

A detector 68 is provided in gas sensing portion 36 to detect radiation C. Detector 68 is positioned within gas sensing portion 36 such that when gas sensing portion 36 and airway adapter 32 are coupled, detector 68 receives at least a portion of luminesced electromagnetic radiation C from luminescable medium 60. Based on the received radiation, detector 68 generates one or more output signals related to one or more properties of the received radiation. For example, the one or more output signals may be related to an amount of the radiation, an intensity of the radiation, a modulation of the radiation, and/or other properties of the radiation. In one embodiment, detector 68 includes a PIN diode. In other embodiments, other photosensitive devices are employed as detector 68. For instance, detector 68 may take the form of a diode array, a CCD chip, a CMOS chip, a photo-multiplier tube and/or other photosensitive devices.

Luminescable medium 60, in response to radiation B from emitter 66, emits electromagnetic radiation C in a substantially omni-directional manner at a wavelength different from that of the electromagnetic radiation provided by the emitter. The intensity and/or persistence of this luminesced electromagnetic radiation rises and falls according to the relative amounts of one or more analytes, such as oxygen, included in the body of gas within gas flow path 50. In one embodiment, oxygen causes a modification of the intensity and/or persistence of luminescent radiation B by quenching the luminescence reaction. As the concentration of oxygen increases, the modification of the intensity and/or persistence of luminescent radiation C decreases. In one embodiment, luminescable medium 60 is formed as a luminescent film. For example, both of the incorporated '896 and '402 patents disclose films that may be employed as luminescable medium 60.

Based on the output signal from gas sensing portion 36, processing portion 38 determines information related to one or more properties of one or more analytes or constituents included in the gas disposed within flow path 50. In the illustrated exemplary embodiment, processing portion 38 includes a processor 70 that controls emitter 66 and receives the signal from detector 68. Processor 70 uses the signal from detector 68 to determine the oxygen concentration as discussed in detail below. Although not shown, processor 70 and/or processing portion 38 may include other components typically used to monitor gas constituents, such as memory (RAM, ROM).

As shown in FIG. 3, the present invention contemplates that processing portion 38 includes an input/output device 72 or devices for providing an output of processor 70 in a human perceivable format. In an exemplary embodiment, input/output device 72 is a monitor or display that visually indicates the oxygen concentration to the user. The present invention also contemplates that input/output device 72 includes communication elements, such as terminals, transceivers, modems, etc. for communicating an output of processor 70 to a remote location. This can be done wirelessly, via a hardwire communication system, or using any combination thereof.

Figure 4:
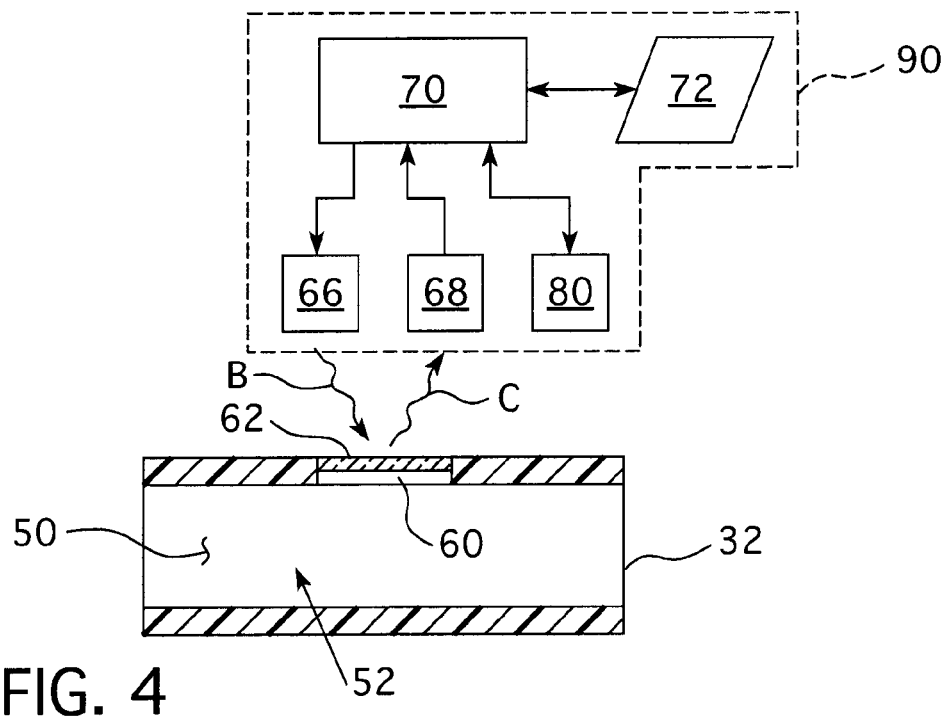
FIG. 4 is a schematic view of the components of a second embodiment of a gas sensing system according to the principles of the present invention.
Figure 5:
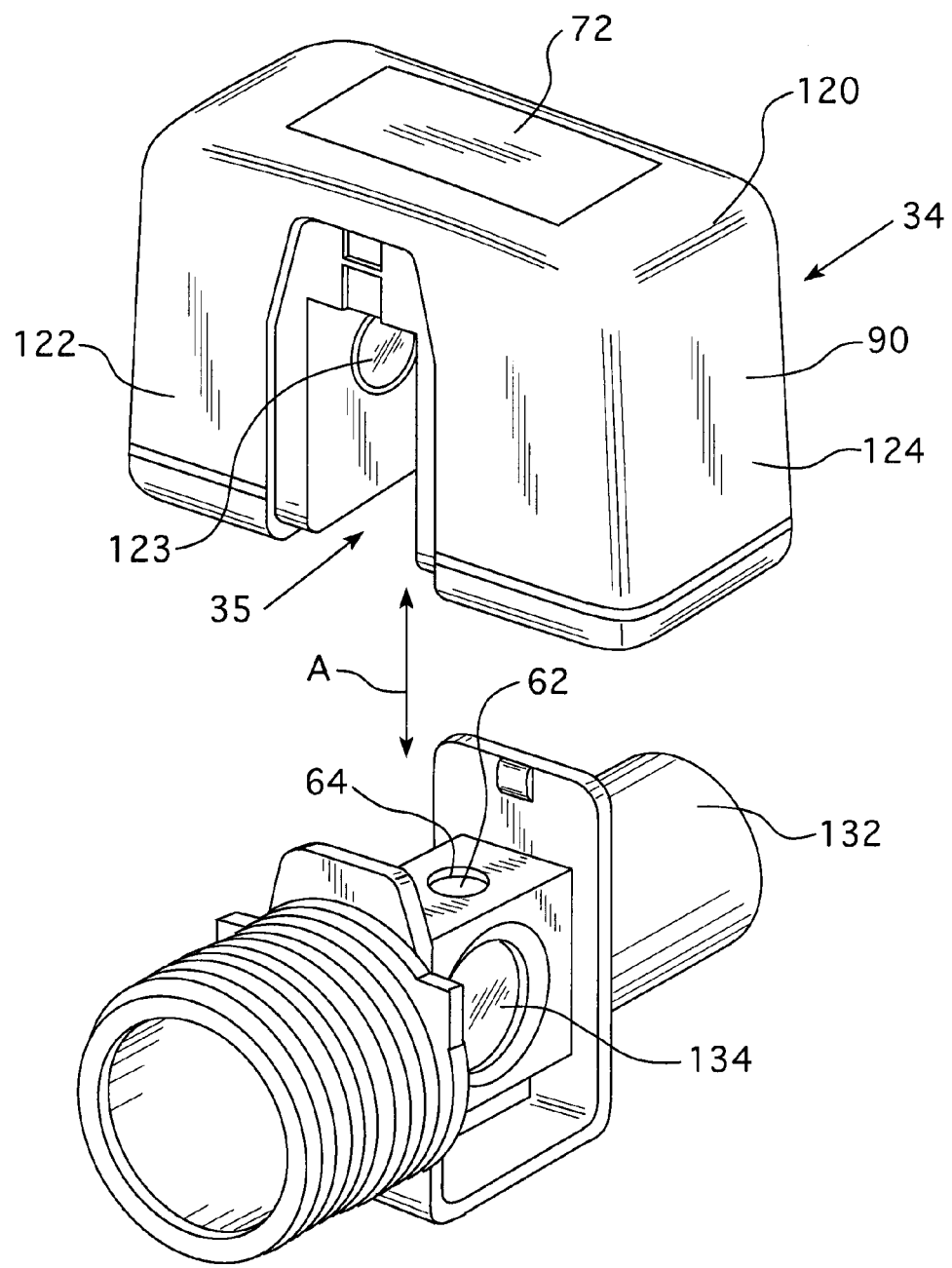
FIG. 5 is a perspective view of an airway adapter and gas sensor according to a third embodiment of the present invention.

In the embodiments of FIGS. 1-3, gas sensing portion 36 and processing portion 38 are separate structures that contain their respective components. The present invention also contemplates that these two portions can be combined into a common gas sensing/processing portion 90, as shown schematically in FIG. 4 and in FIG. 5. That is, all of the components necessary to detect, monitor, determine, display, and communicate information pertaining to the gas concentration, such as VO₂ can be provided in the sensor head 90 that attaches to airway adapter 32. An example of a sensor head 90 having such functionality is shown in FIG. 5 and is disclosed, for example, in U.S. patent application Ser. No. 11/368,832 (publication no. US-2006-014078-A1), the contents of which are incorporated herein by reference.

The present invention contemplates that additional components can be used in gas sensing portion 36. For example, one or more filter elements can be positioned within the gas sensing portions, e.g., between luminescable medium 60 and detector 68. Such filter elements are typically designed to prevent electromagnetic radiation that is not emitted by the luminescable medium from becoming incident on the detector. For instance, in one embodiment, the filter elements are wavelength specific and permit luminescence radiation C to pass therethrough to become incident on detector 68 while substantially blocking radiation with other wavelengths.

Other components that can be used in gas sensing portion 36 include a reference detector and a beam splitting element that directs a portion of the radiation propagating toward detector 68 onto the reference detector. One or more output signals generated by the reference detector may be provided to processor 70 and used as a reference to account, and compensate, for system noise (e.g., intensity fluctuations in emitter 66, etc.) in the signals generated by detector 68.

In some implementations, gas sensing portion 36 may include one or more optical elements (not shown) to guide, focus, and/or otherwise process radiation emitted by emitter 66 or provided to detector 68. For example, one or more lenses may collimate the radiation in a selected direction. As more particular examples, both of the incorporated '896 and '402 patents disclose the use of optical elements that process radiation emitted by an emitter similar to emitter 66.

The present invention further contemplates using a thermal capacitor to maintain luminescable medium 60 at a substantially constant operating temperature to reduce or eliminate inaccuracies in gas measurement system 30 attributable to variations in the temperature of the luminescable medium. Thus, the thermal capacitor is any device that accomplishes this function, such as a heater controlled in a feedback fashion based on an output of a temperature sensor, a heat sink, or the like. Examples of suitable thermal capacitors in the form of heating elements are disclosed in U.S. Pat. No. 6,888,101 and in U.S. patent application Ser. No. 11/069,114 (publication no. US-2005-0145796-A1), the contents of each of which are incorporated hereby by reference.

In the embodiment illustrated in FIGS. 1-4, a single window 62 is provided on the airway adapter. The present invention also contemplates providing two windows similar to window 62 in the airway adapter. As is shown and described in the '402 patent, the two windows may be disposed in airway adapter 32 opposite from each other to enable electromagnetic radiation to pass through the adapter. In this embodiment, a detector 68 may be positioned on an opposite side of the airway adapter from emitter 66 when sensor.

The present invention also contemplates that airway adapter 32 can include other one or more additional gas measuring and/or sensing components. These other sensing components are schematically illustrated as 80 in FIG. 3. Examples of such sensors includes temperature, light, sound, humidity, pressure, flow, and gas concentration sensors. Such sensors can be used to monitor the flow of gas, gas sensing portion 36 or both. For example, a temperature sensor can be provided in housing 37 to detect overheating in the housing. A temperature sensor can also be provided to detect the temperature of the gas flowing in the airway adapter.

FIG. 5 illustrates a gas monitoring system that includes both a carbon dioxide ($CO_2$) concentration detecting capability and an oxygen ($O_2$) concentration detecting capability. The oxygen concentration detecting system corresponds to the luminescence quenching technique discussed above and includes a luminescable material disposed on window 62 of an airway adapter 132. The $CO_2$ monitoring system is an absorption type gas (analyte) detection system in which energy is transmitted from an emitter (not shown) disposed on one leg of a housing 120 (such as leg 122). A window 123 is shown on an interior surface of leg 122 from which the energy exits housing 120. The energy is provided to a first window (not shown) defined in the airway adapter. It passes through a gas sample (the gas flowing through gas flow path 50), and out a second window 134 also defined in the airway adapter generally opposite the first window. The energy exiting the sample site via second window 134 is measured by a detector (not shown) provided in second leg 124.

As known in the art, the signal from the detector is used to determine the gas (analyte) concentration. For example, it is known to use the output of this type of absorption system to detect the amount of $CO_2$ in the gas passing through the airway adapter, which is used to determine the amount of expired CO2 ($Fe_{CO2}$) and the amount of inspired $CO_2$ ($Fi_{CO2}$). The signal from the detector can be processed by a processor provided in housing 120 or sent wirelessly or via a hardwire 48 to a separate processing portion. In this illustrated embodiment, the processing portion is incorporated into housing 120 and the resultant analyte measurement is shown on display 72.

In a similar fashion, the present invention further contemplates that the airway adapter can be configured to include a flow sensing system to measure the flow or flow rate of gas passing through the airway adapter. The flow rate is used to determine the amount of analyte passing through the airway adapter over a given period of time or during a respiratory cycle or phase thereof.

One type of flow sensing system suitable for use in this embodiment of the present invention is a pneumotach type of flow sensor. Such a flow sensor includes a flow element (not shown) that is disposed in the gas flow path so as to create a pressure drop in the flow of gas along the gas flow path. The pressure drop created by the flow element is measured and used to determine the flow rate.

Figure 6A:
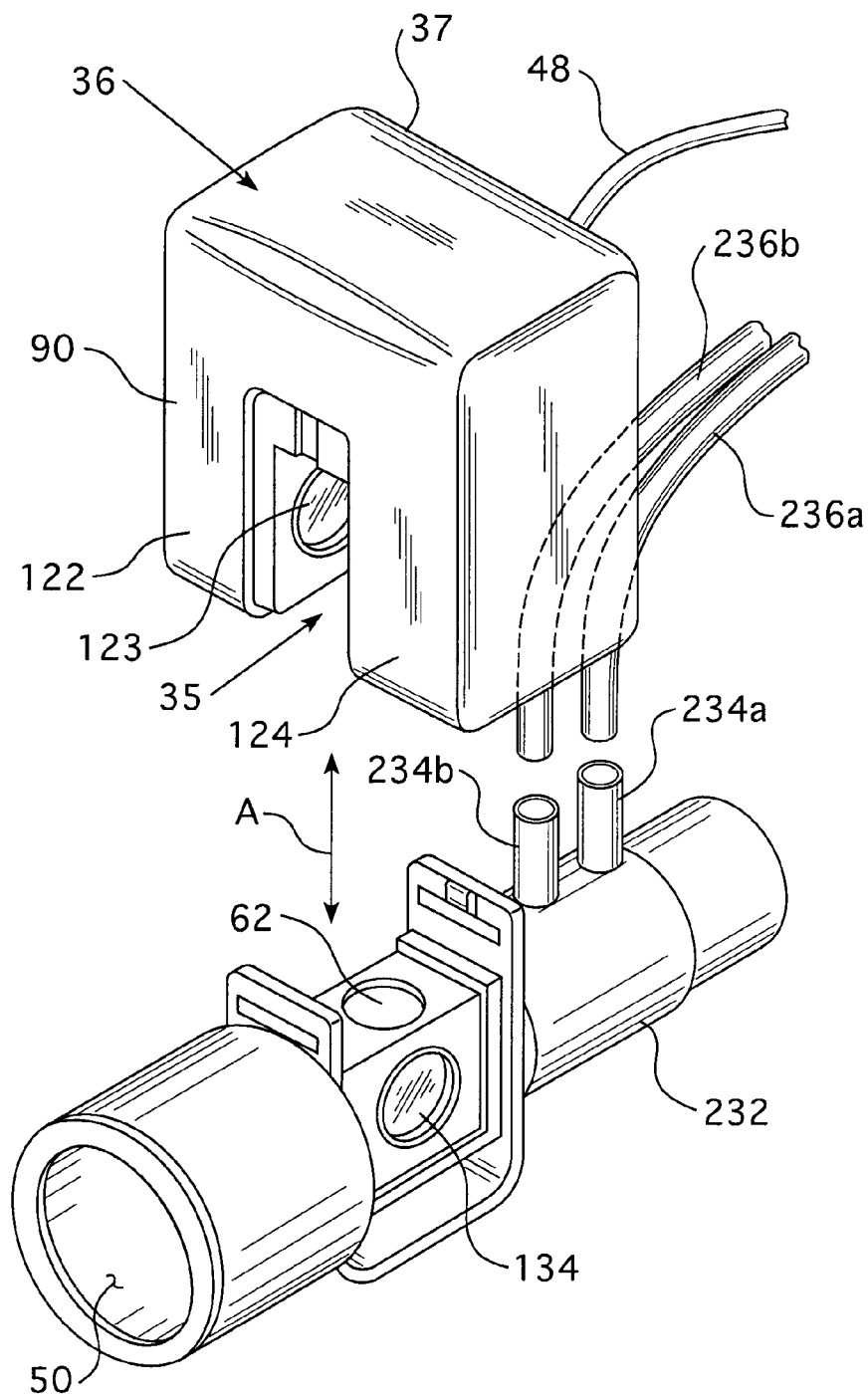
FIG. 6a is a perspective view of an airway adapter and gas sensor according to a still further embodiment of the present invention.
Figure 6B:
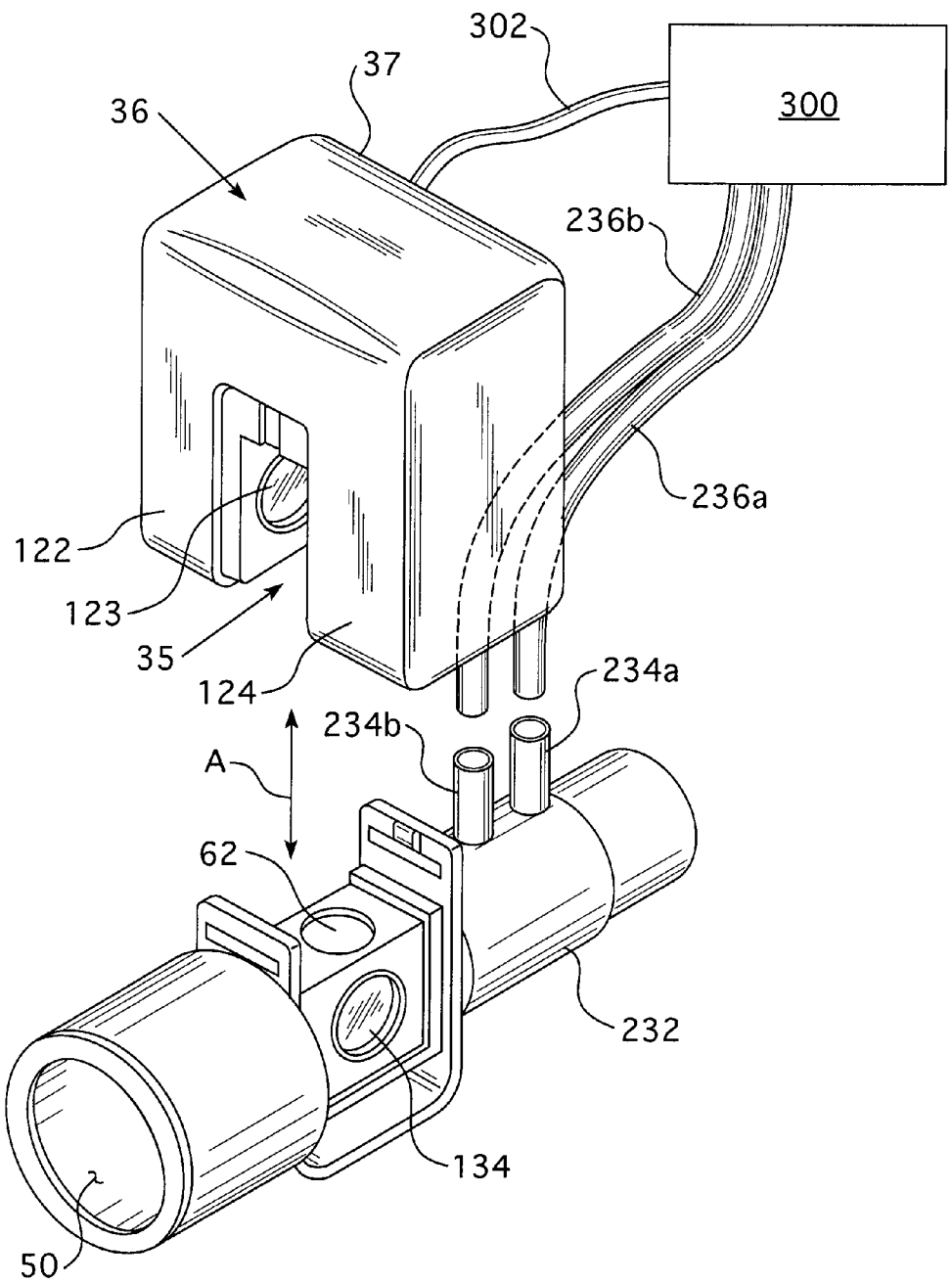
FIG. 6b is a perspective view of an airway adapter and gas sensor according to yet another embodiment of the present invention.

FIGS. 6a and 6b illustrate an airway adapter 232 having such a flow sensing capability. It should be noted that airway adapter also has an $O_2$ and $CO_2$ sensing capability using the techniques discussed above. Airway adapter 232 includes a pair of ports 234a and 234b that are provided on each side of the flow element contained within the airway adapter. These pressure sensing elements allow the pressure drop across the flow element to be measured so that the flow of gas through the airway adapter can be measured quantitatively. For example, a pair of tubes or pneumatic hoses 236a and 236b can be coupled to ports 234a and 234b to and to a pressure sensor or sensors in processing portion 38 (see FIG. 1). The pressure sensors measure the pressure drop and this output is used to determine the flow through the airway adapter.

In the embodiment illustrated in FIG. 6a, the additional flow sensing function is not contained in housing 37, which also contains at least some components of analyte sensing system. However, the present invention also contemplates that the flow sensing elements, such as the pressure sensor(s) and processor can be contained in housing 37. In which case, ports 234a and 234b would be coupled directly to the housing. In the embodiment illustrated in FIG. 6a, the flow element is provided on one side of the gas measurement site. The present invention also contemplates using the gas measurement site to create the pressure drop. In which case, ports 234a and 234b would be provided on either side of the gas measurement cite. Such a configuration is taught, for example, in the '660 patent, the '389 patent, and the '451 application.

In certain embodiments, a mainstream oxygen sensing system is provided that takes into account the effect of the change in temperature and humidity of expired gases in comparison with temperature and humidity of inspired gas (due to the inspired gas not being exposed to body temperature and saturated conditions). This change in temperature and humidity results in measured increases in volume of the exhaled gas and can be accounted for by correcting the inspired oxygen fraction measured. Correction of the inspired oxygen fraction in this manner can result in improved accuracy of oxygen consumption measurement using the Haldane transform. Systems and methods for achieving such improvements in accuracy are described in U.S. patent application Ser. No. 11/948,080, the entire contents of which is hereby incorporated herein by reference.

Figure 7:
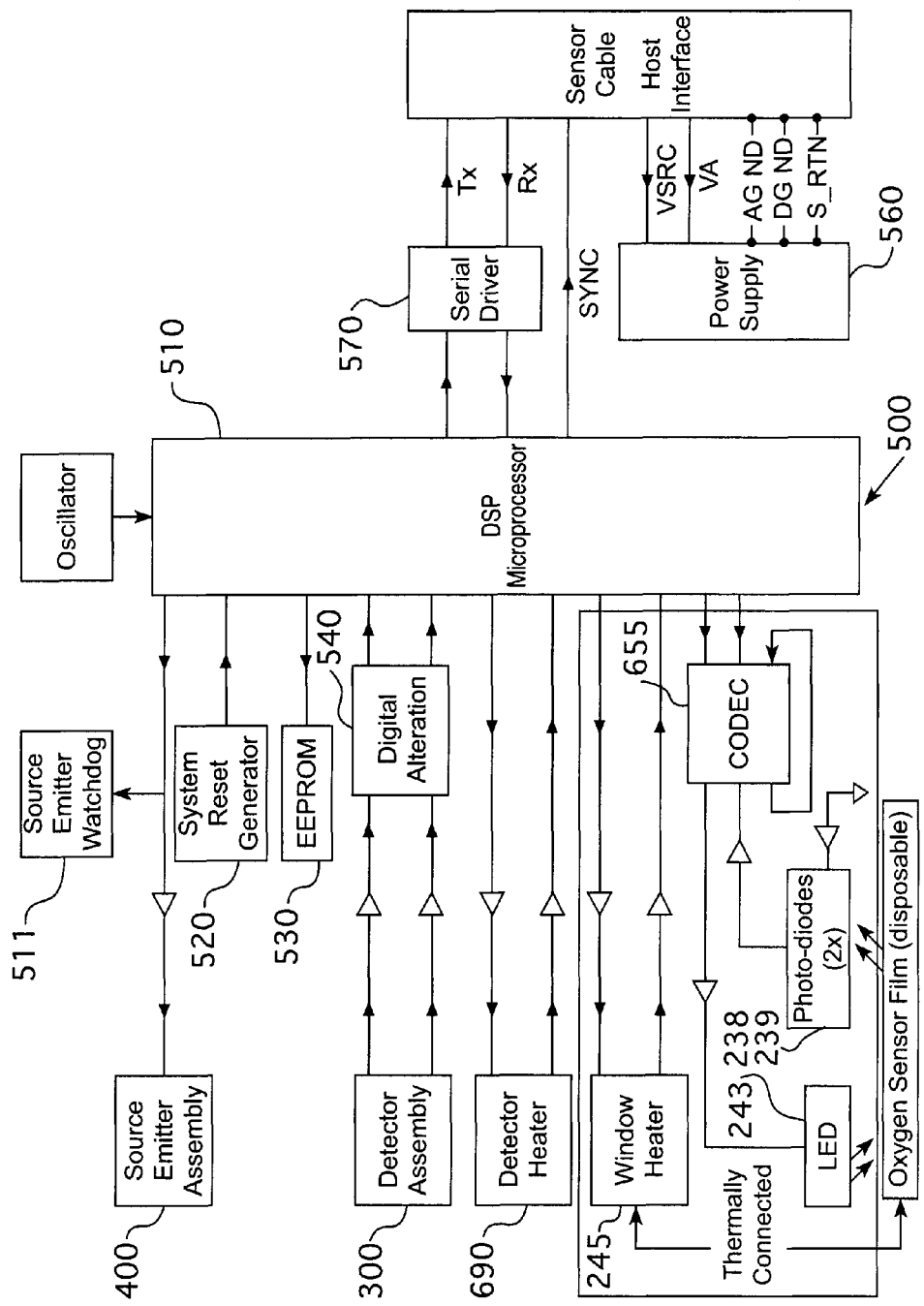
FIG. 7 is a block diagram of a gas measurement system according to aspects of the present invention.
Figure 8:
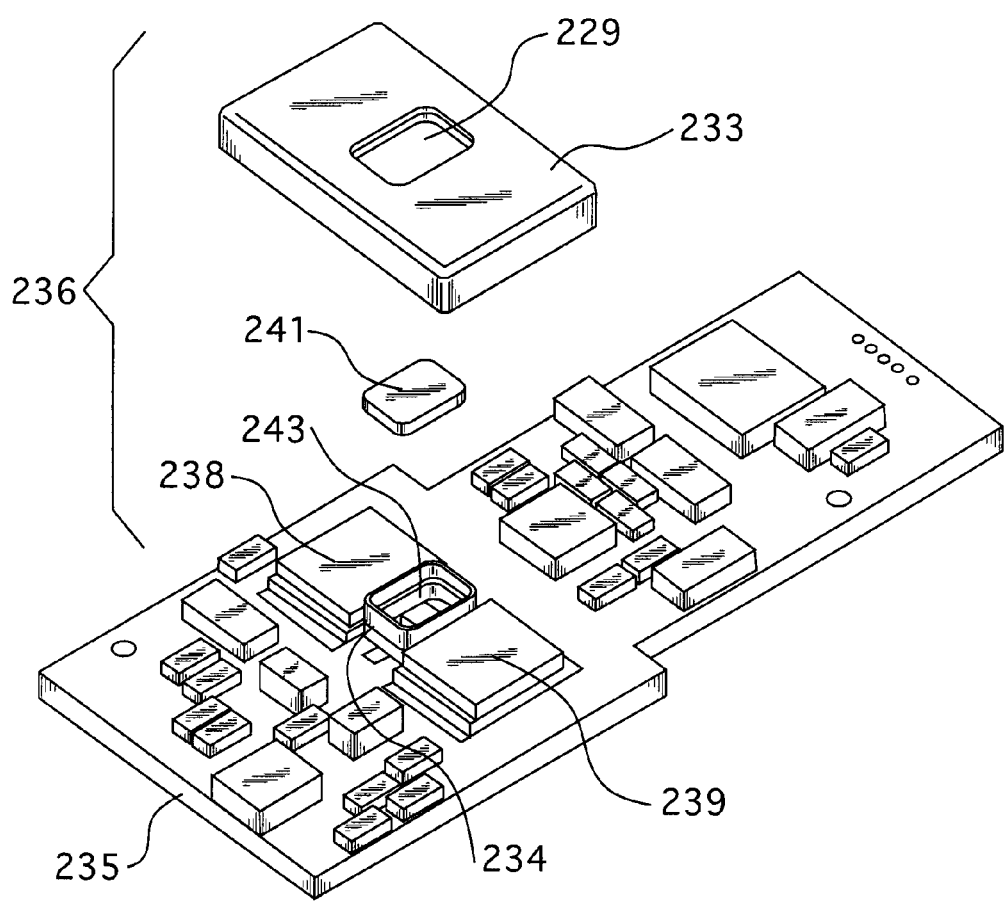
FIG. 8 is an exploded view of luminescence quenching measurement circuit board in a gas measurement system.

Referring to FIGS. 7 and 8, FIG. 8 provides a perspective exploded view of a luminescence quenching measurement circuit board such as is described in U.S. patent application Ser. No. 11/165,670 (publication no. 2006-0009707-A 1) ("the '670 application"), which application is incorporated herein by reference in its entirety. The exemplary luminescence quenching optical system 236 includes an excitation source 243, detectors 238 and 239 positioned on each side of excitation source 243, detector filter 233, optional excitation source filter 241, and shield 234. All are disposed on the same plane permitting size and weight to be reduced. An exemplary excitation source comprises a green light emitting diode. Excitation source 243 and detectors 238 and 239 are separated from each other by electrical shielding and optical filters. An exemplary detector consists of a photodiode. It is to be understood that the present invention contemplates providing a ring of photodetectors surrounding or partially surrounding source 243. This ring can be a single detector or a plurality of detectors and can have any suitable pattern, such as circular, square, triangular, rectangular, etc.

Detector filter 233, in the exemplary embodiment, is a rectangular filter structure with an aperture 229 through which the radiation from the excitation source is emitted. The optical properties of detector filter are such that the wavelengths of radiation related to the luminescence quenching of the sensing film/chemistry in response to contact with the gas or gases to be measured are substantially transmitted through the filter and radiation not related to that interaction is substantially not transmitted through the filter. The detector filters may be band pass, high pass, low pass, or any other filter type known in the art. In addition, an optional excitation source filter 241 may be used to limit the emission of radiation outside the wavelengths of radiation to which the sensing film is excited by thereby preventing unwanted wavelengths from reaching the sensing film.

The sensing film that is sensitive to a gas of interest is preferably disposed on a plane that is parallel to, and displaced from, the first plane of the exemplary luminescence quenching optical system 236. To minimize unwanted interaction between the excitation source and detectors, shield 234 is placed around excitation source. The internal surface of shield 234 in the exemplary embodiment is substantially reflective for the radiation emitted by the excitation source thereby serving two purposes. This allows it to redirect the extraneous light back towards the sensing film improving the efficiency of the system. Additionally, excitation sources, such as LEDs, emit light into a larger angle than that subtended by the sensing film. The shape of the shield is preferably designed to block the light from reaching the detectors directly and influencing the luminescence measurement.

In the exemplary embodiment shown, the radiation emitted from the excitation source 243 is transmitted through filter 241 and through aperture 229 and is incident on the sensing film. In certain embodiments, aperture 229 may include a domed window (not shown). Based on the concentration of oxygen, the sensing film emits radiation at a different wavelength, which is transmitted back through aperture 229 and filtered by detector filter 233 and measured by the two detectors disposed within detector filter 233.

Additionally, an index matching layer (not shown) may be optionally positioned between the detectors and detector filter to minimize reflective loss. Radiation from the sensing film is emitted in all directions and only a small fraction of the emitted radiation is directed towards the detectors. Due to Fresnel reflections, this radiation is further attenuated at every interface along the optical path. Thus, filling the air gaps with a material, such as an index matching material, allows this reflective loss to be minimized.

A heater flex circuit can be electrically interfaced to luminescence quenching measurement circuit board 235. A control algorithm, typically executed by an embedded processor such as a PID controller, serves to regulate the temperature typically between 40° C. and 50° C. and within a ±0.02° C. tolerance. The detector heater can be powered by a +5 V DC supply, which may also used to power analog and digital circuitry regulators. FIG. 7, for example, contemplate providing a window heating system that includes a temperature sensing component and a heating component 245. Electronics on circuit board 235, in conjunction with the microprocessor 70, for example, control the delivery of energy to the heating component.

A control algorithm within microprocessor 70 uses the sensed temperature maintains the temperature of the heating element to a temperature sufficiently above ambient temperature within the airway adapter. A decoder and encoder 555 with integrated digital-to-analog converters and analog-to-digital converters can be interfaced with microprocessor 70 to modulate excitation source 243 using the output of detectors 238 and 239 in such a manner to perform phase-based measurements of lifetime. Serial driver 570 can be used to communicate bi-directionally using a transmit and receive line denoted Tx and Rx respectively. Power supply 560 receives power from VSRS and VA lines with signal return and a digital and analog ground provided. Temperature control or compensation is required because the amount of luminescence emitted from the sensing film is influenced by temperature.

To maintain a constant temperature at the film, window heater (not shown) thermally communicates to the flat side of a window in the aperture 229 which, by convention, is sapphire. This heater keeps the window in aperture 229 at a constant temperature which in turn maintains the temperature of the sensing film. The window heater may be designed into a ring shape to remain outside of the optical path. The window in aperture 229 can be domed instead of flat to improve thermal contact with the sensing film. The close contact between these two components and the curved profile also have the effect of improving the amount of light transmitted through to the sensing film and back towards the detectors. As noted above, an exemplary embodiment of a luminescence quenching optical system suitable for use in the present invention is disclosed in the '451 application.

It will be appreciated that the flow of gases past aperture 229 may cause variations in temperature corresponding to changes in the rate and direction of flow of the gases. These variations in flow characteristics may induce corresponding variations of instantaneous temperature of the oxygen sensing film, which, while in contact with the window in aperture 229, is also in close intimate contact with the flowing gases. Thus, temperature gradients that exist between the thermal sensing element, the window, and the oxygen sensing film will fluctuate during rapid changes in gas flow rate and direction during a respiratory cycle. Electronics on circuit board 235 may be incapable of responding to such temperature variations with sufficient speed to prevent errors in measurements because the instantaneous temperature of the sensing film is not precisely the same as the temperature of the thermal sensing element. For example, tracking changes in respiratory gas constituents may be subject to interference due to the cooling effects of the cyclical flow past the sensor of large volumes of gas. Because the cooling effects of the cyclical flow of respiratory gases past the sensor generally results in a small temperature gradient between the regulated window temperature at the location of the thermal control sensing element and the window film in contact with the flowing gas, the steady-state (or DC average) temperature of the oxygen sensing film can vary slightly with the average cyclical volume of the respiratory gas, and also with the temperature of the gas Certain embodiments of the present invention can mitigate errors associated with the interaction of sensing elements and gas streams and, in particular, associated with the problem of respiratory gas cooling effects on certain types of mainstream sensing devices used in conjunction with spirometry. Consistent with certain aspects of the present invention an accurate instantaneous stream of oxygen measurements can be attained using a sensing element in contact with the respiratory gasses, even though the temperature of the sensing element may be impacted by the temperature fluctuations that can occur in a mainstream respiratory monitoring application. For example, and as described above, if a sensor uses an oxygen sensitive element operating under the principle of fluorescence quenching located within the respiratory gas stream, the oxygen sensitive element should be maintained at a constant temperature. Because such an oxygen sensitive element must be in direct contact with the flowing respiratory gas, it may be difficult, complicated, or impractical in some instances to prevent the temperature of this element from fluctuating as respiratory flow changes. Even in embodiments in which various temperature control elements may be used to reduce temperature fluctuations, some fluctuations may exist in any event.

Therefore, certain embodiments of the present invention provide methods for correcting errors in the oxygen measurement caused by these temperature fluctuations, when such sensor is used in conjunction with a flow sensor in order to estimate oxygen consumption and related or other metabolic parameters. These methods include utilization of a measurement of instantaneous respiratory flow rate combined with estimates of gas temperature and composition to estimate the sensor cooling effects from which a flow based time varying compensation factor is derived. Compensation factors can then be applied to a measurement signal obtained from a sensor to obtain a corrected measurement signal. Correction factors may be maintained in storage and associated with a range of pressure and flow conditions. Furthermore, processing logic may account for skew between signals measuring pressure, flow rate and oxygen content by aligning skewed signals to a common time base prior to applying correction factors.

In certain embodiments, correction factors are obtained empirically and a processor is preconfigured to apply the corrections factors based on known characteristics of the sensor type. In some embodiments, the processor utilizes stored correction factors based on a history of prior measurements obtained during operation of a particular device. For example, a processor may monitor temperature of a window in aperture 229, gas flow rate, and pressure over a period of time to determine relationships between changes in flow characteristics and changes in temperature of the window in aperture 229. Thus, the processor may more accurately model the performance of temperature compensation electronics in response to variations in flow rate and pressure, and provide more optimal compensation of a measurement signal as a result.

In one embodiment, using a sensor such as a luminescent quenching oxygen sensor, which is sensitive to gas temperature, a film heater may be used to maintain the heat of the sensing film at a generally constant temperature. Gas flow within the airway adaptor causes the film to cool, leading to lower oxygen partial pressure measurements.

Although feedback control systems for the film heater may be adequate to compensate for constant gas flow, it may not adequately compensate for rapid changes in the flow rate that can be observed during breathing. In accordance with one aspect of the present invention, a simple compensation algorithm may be deployed that uses the flow signal measured by a multi-parameter processor or monitor 300 (see FIG. 6*b*) to compensate for a flow-induced error in the oxygen signal. Such multi-parameter monitor 300 may measure patient generated signals, and has a flow sensor portion for sensing flow rate into and out of the patient, a pressure sensor portion for sensing patient airway pressure, an oxygen concentration determining portion for measuring airway oxygen concentration (partial pressure), and a $CO_2$ concentration determining portion for measuring $CO_2$ concentration. In addition, the monitor may also have a barometric sensing portion for measuring barometric pressure. In an exemplary embodiment, such as that shown in FIGS. 4 and 6*b*, processor 70 is contained within gas sensing portion 36 and communicates with multi-parameter monitor 300 via communication link or line 302, which can be hard wired or wireless. Monitor 300 receives the gas measurement signals, e.g., $O_2$ and/or $CO_2$ measurement signals, through line 302. In addition, monitor 300 receives pressure information through lines 236*a* and 236*b*.

Alternatively, processor 70, as well as additional processors may be contained in monitor 300. It should be appreciated that each of the aforementioned sensors, sensing portions, or determining portions may communicate with or be considered to be an integral part of a sensing system that includes one or more processors for processing the sensed physical parameters (e.g., flow rate, pressure, concentration, etc.). The location of such processors can be varied, from one processor to another, or all processors may be integrated into one.

Certain embodiments of the invention implement the compensation algorithm in conjunction with a set of compensation parameters. Compensation parameters may be obtained theoretically or by modeling, but can be more easily obtained empirically. For example, a ventilator (or syringe) can be used to ventilate a test lung filled with air such that flow and pressure can be changed while maintaining a constant concentration of oxygen. Oxygen pressure and flow signals can be collected from a monitor, such as multi-parameter monitor 300, that is configured to execute data collection software. Data collected for various flow rates and pressures can be analyzed to derive a set of flow compensation parameters. In certain embodiments, optimal results may be obtained when the compensation algorithm is applied to pressure-compensated oxygen signals.

In one embodiment, the total airway pressure (defined as the sum of the airway pressure and barometric pressure) that is in the breathing circuit (in absolute pressure units) is measured by monitor 300 concurrently with each oxygen measurement. A pressure correction factor is computed as the ratio of the total patient airway pressure to barometric pressure, and is applied to the oxygen value (e.g., raw value) measured in pressure (e.g., mmHg, kPa) or volume units.

Thus, the pressure compensated oxygen measurement (% oxygen$_{\_pressure\_comp}$) may be expressed as follows:

$$\% \text{ oxygen}_{\_pressure\_comp}[n] = \% \text{ oxygen}_{\_raw}[n](\text{total airway pressure}[n]/\text{barometric pressure}), \quad (5)$$

where "[n]" is an $O_2$ signal sample at time [n], "% oxygen$_{\_raw}$" is the non-pressure compensated oxygen signal, and "total airway pressure" is the sum of the airway pressure and the barometric pressure. If necessary, the pressure signal used in the pressure compensation is delayed and low pass filtered.

In the case of a mechanically ventilated patient, the airway pressure may reach values as high as 120 cm $H_2O$ and vary as much as 50 cm $H_2O$ or more over the breathing cycle. Thus, this variation in pressure within the breathing circuit is desirably accounted for as indicated above.

In another embodiment of the present invention, the measured flow is used in combination with the pressure compensated oxygen measurement to compensate the oxygen measurement signal with greater accuracy. In an exemplary embodiment, a flow compensation equation can be stated as follows:

$$\% \text{ oxygen}_{\_flow\_compensated}[n] = \\ \% \text{ oxygen}_{\_pressure\_compensated}[n] * (1.0 + K_X * flow_{filtered}[n]),$$

where "% oxygen$_{\_flow\_compensated}$[n]" is the flow compensated percent oxygen for the current (nth sample), $K_X = K_I$ during inspiration and $K_X = K_E$ during expiration, "$K_I$" is the compensation factor applied for inspiratory flow, "$K_E$" is the compensation factor applied for expiratory flow, and "flow$_{filtered}$[n]" is the flow signal appropriately delayed and low-pass filtered to match the time response of the oxygen signal. In one example, flow compensation factors were optimized as $K_I = 0.00012$, and $K_E = -0.00030$. Typically, the flow signal used in the flow compensation is delayed and low pass filtered.

These compensation factor values were determined experimentally. It is contemplated that embodiments in which $K_I$ is between 0.00006 and 0.00018, and in which $K_E$ is between −0.00020 and −0.00040 may be desirable. However, these are non-limiting examples. In other embodiments, different compensation equations may be used.

In addition, while in the above embodiment the flow signal is filtered (slowed) to match the frequency response of the $O_2$ signal, in some embodiments, where the $O_2$ signal is faster than the flow signal, the $O_2$ signal can be filtered to frequency match the flow signal. Such processing and compensation of signals are done by the processor in monitor 300, although it can also be performed by a processor within the gas sensing portion 36.

Figure 9:
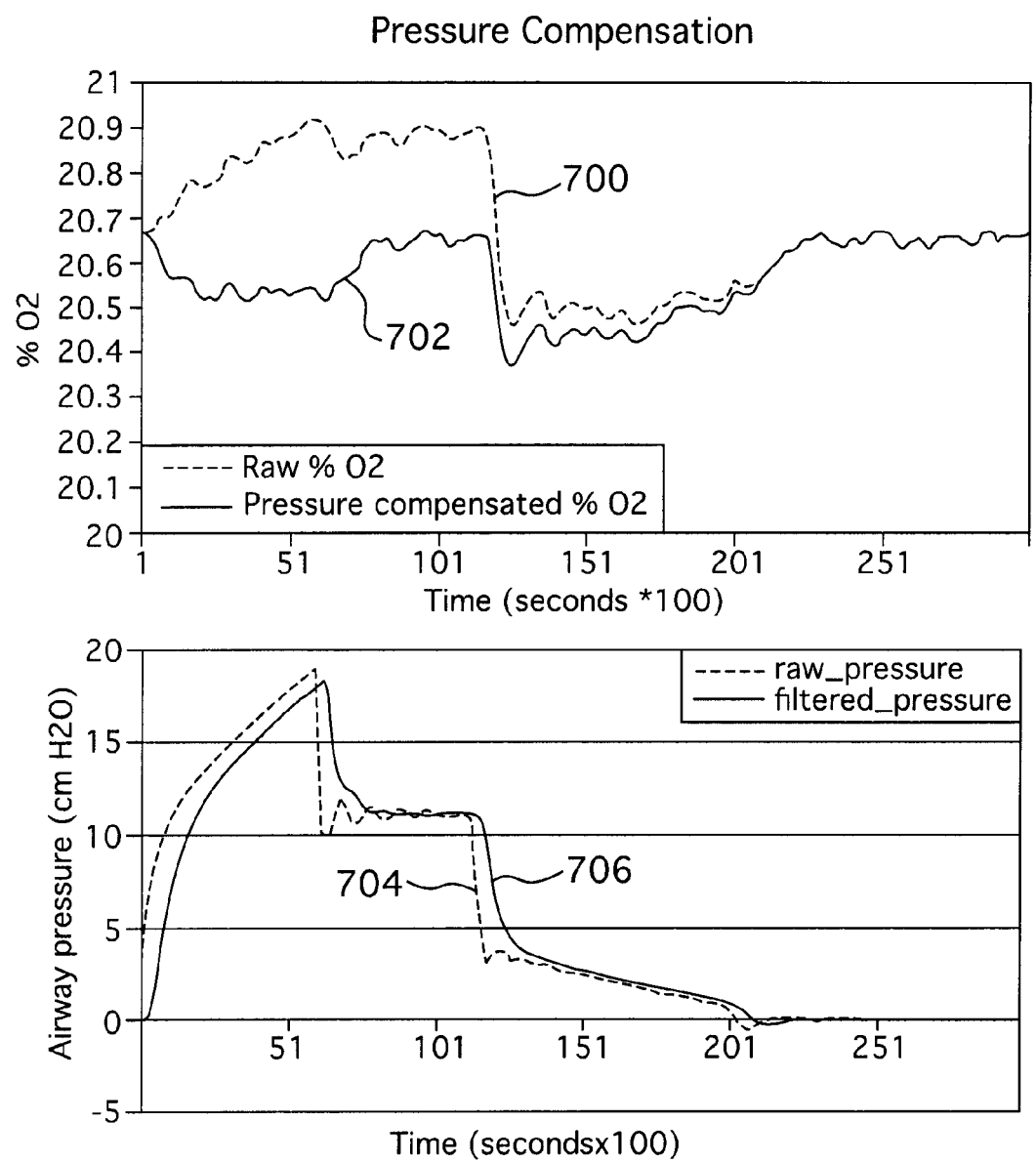
FIG. 9 includes charts showing the relationship between oxygen content and gas pressure over time.
Figure 10:
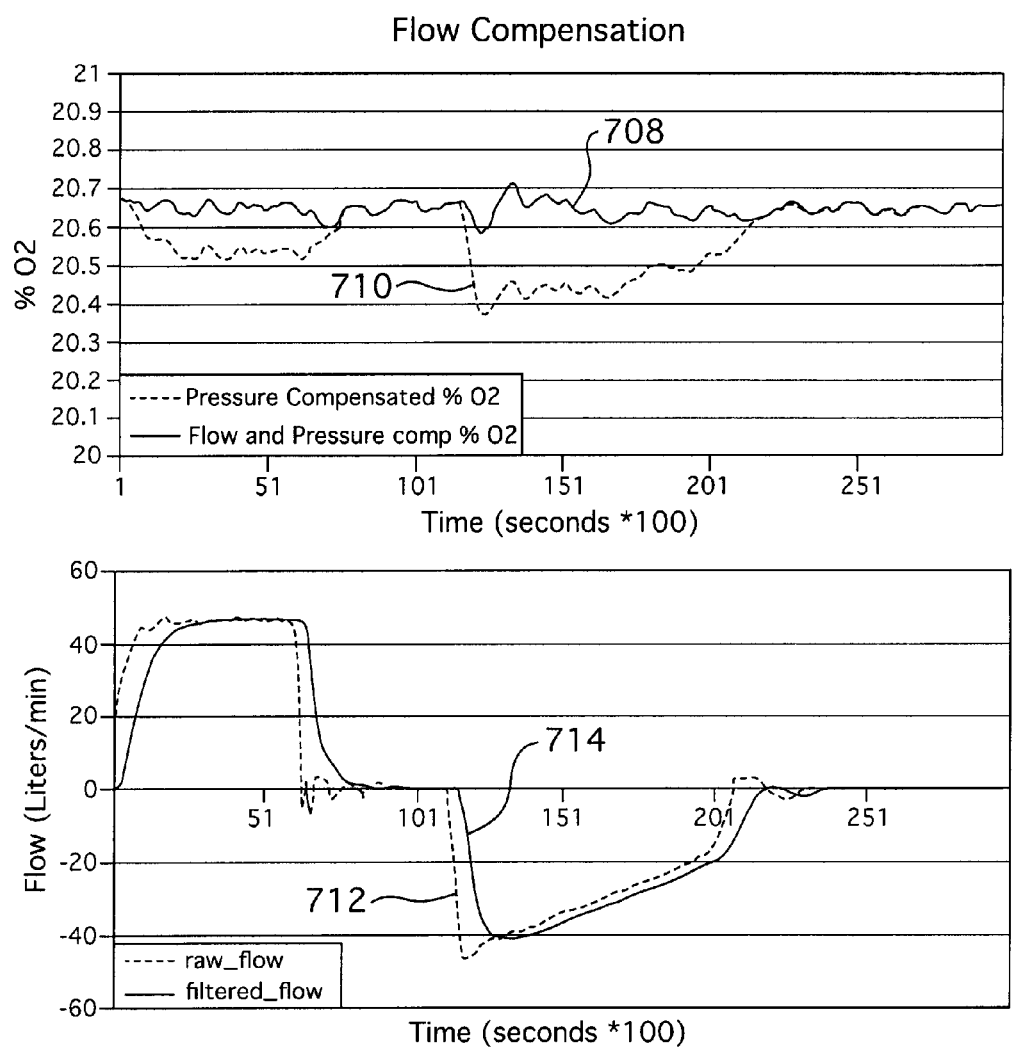
FIG. 10 includes charts showing the effects of compensating for flow and pressure according to aspects of the invention.
Figure 11:
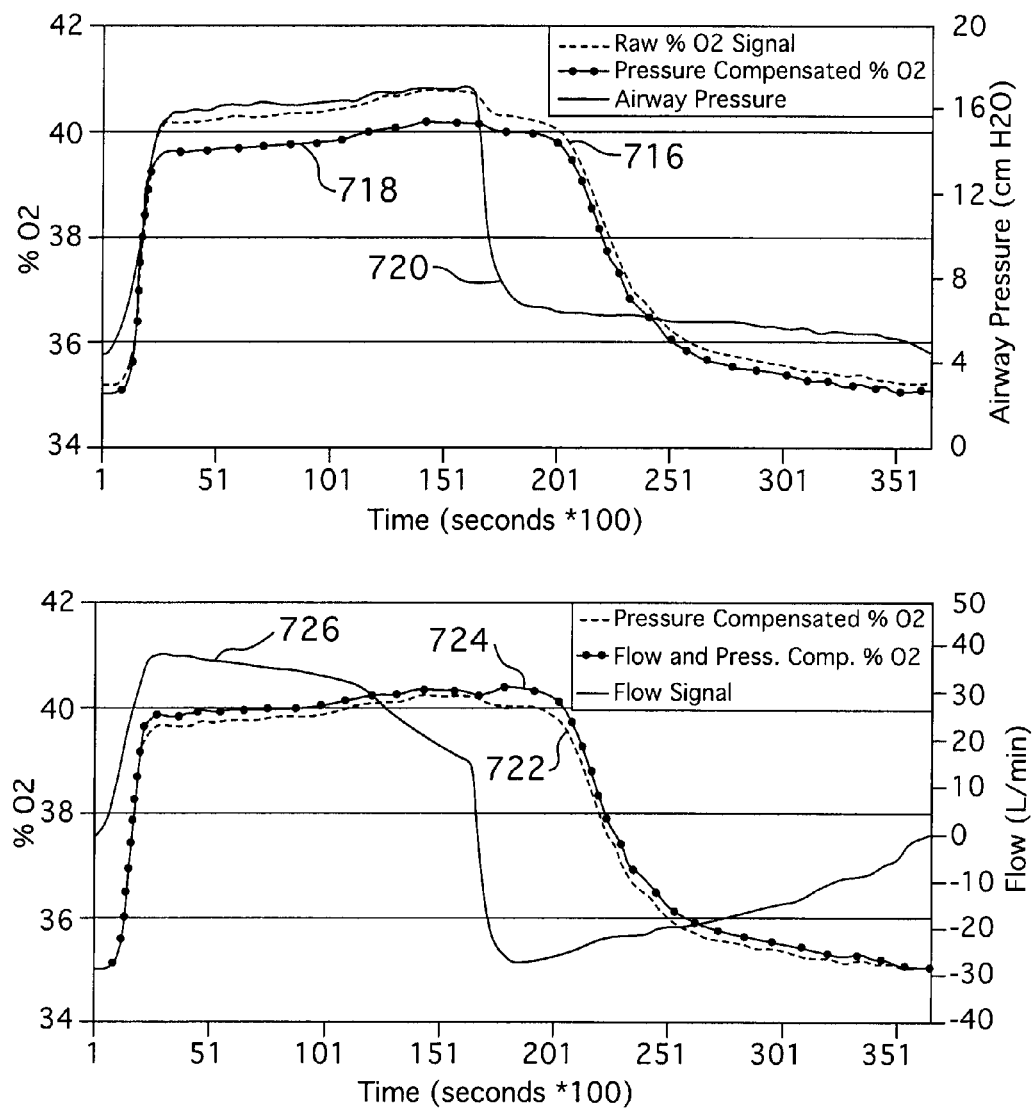
FIG. 11 includes charts showing the effects of compensating for flow and pressure according to aspects of the invention.

FIGS. 9-10 provide graphical representations showing the effect of applying both pressure and flow compensations in a test environment similar to that described above. The data underlying the charts were collected by using a ventilator to deliver room air gas into a test lung completely filled with air. The upper plot of FIG. 9 includes plots corresponding to a raw uncompensated oxygen signal 700 and a pressure compensated oxygen signal 702 (both shown as a measure %). The lower plot of FIG. 9 shows the corresponding raw airway pressure signal 704 and a filtered airway pressure signal 706. The upper plot of FIG. 10 includes plots corresponding to a pressure compensated oxygen signal 708 compared to a pressure and flow compensated oxygen signal 710. The lower plot of FIG. 10 shows raw flow rate 712 and filtered flow rate signals 714. FIG. 11 provides graphical representations showing the effect of applying both pressure and flow compensations in data from an actual intensive care unit patient. The upper plot of FIG. 11 shows raw oxygen 716 and pressure compensated oxygen signals 718 in relation to measured airway pressure 720. The lower plot of FIG. 11 shows a pressure compensated oxygen signal 722, a flow and pressure compensated oxygen signal 724, and a measured airway flow rate signal 726. The primary purpose of filtering the flow and pressure signals is to match the phase and/or frequency response of these signals with the gas signal (e.g., the oxygen signal). It will be appreciated that low-pass filters can also be applied to the signals and are effective in removing noise-like higher frequency variations in the signals. It will be appreciated that optimal results are obtained when compensation for both flow and pressure is implemented.

Figure 12:
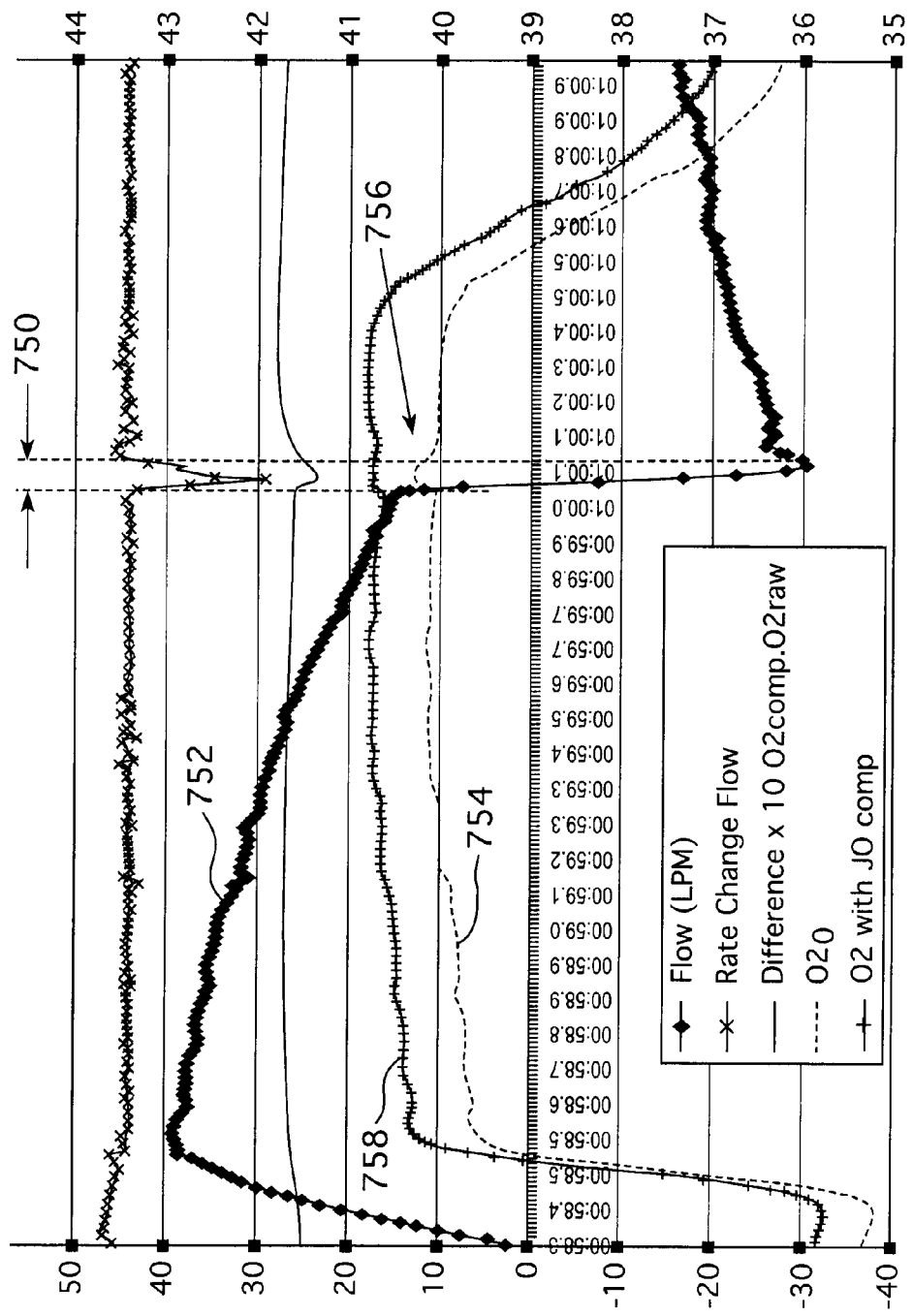
FIG. 12 is a chart of pressure, flow and oxygen content measured in an operational system.

Referring to FIG. 12, compensation parameters obtained from test subjects is generally consistent with the graphs of FIGS. 8-10. FIG. 12 illustrates a flow signal 752 and a raw oxygen signal 754 during the transition from inspiration to expiration. During a transition period 750, when the flow direction changes corresponding to a change from inhalation to exhalation, a "spike" 756 may be observed in the measured oxygen. The spikes occurring at these transitions may be removed from consideration using a combination of low pass filtering and transition compensation parameters and/or the flow or pressure compensation techniques discussed above. FIG. 12 shows a compensated oxygen signal 758 (which shown is offset slightly from raw oxygen signal 754 so that both waveforms can be represented on the same graph with greater clarity). It can be appreciated that compensated oxygen signal 758 does not include a spike or has a significantly reduced spike as compared to that present in the ray oxygen signal.

In certain embodiments, changes in measurements occurring during the transition period 750 may be ignored and compensation halted. In certain embodiments, compensation parameters are typically applied to the oxygen waveform based on the condition of a low pass version of the flow waveform.

In certain embodiments, compensation factors remain generally constant for various oxygen concentration levels. However, in certain circumstances additional compensation parameters may be varied according to the heat capacity of the flowing gas. It will be appreciated that, because the heat capacity of nitrogen and oxygen are nearly identical, heat capacity compensation is typically required only when the sensor is used in anesthesia where gases, such as $N_2O$, and anesthetic agents, such as desflurane, are present or in use. Additionally, heat capacity compensation may also be employed where gas mixtures such as Heliox (Helium-oxygen) are used (e.g., intensive care).

In addition, the total gas pressure (barometric pressure+ airway pressure) affects the heat capacity of the gas. Adjustments to the compensation factor may be needed to account for changes in heat capacity differences caused by gas composition and/or gas pressure. For example, $K_I$ and $K_E$ would be increased in relation to an increase in the heat capacity based on either user entered gas composition and pressure data, or, alternatively, based on directly measured gas composition or pressure data.

Similar spirometry-based temperature compensations can be applied in other respiratory gas measurement situations where temperature effects can contribute to inaccuracies. For example a mainstream NDIR $CO_2$ sensor measures the gas optically through transparent windows that are heated to prevent condensation. The heated windows affect the temperature of the respiratory gas. Because the measured gas temperature is affected by the flow rate of the gas as it passes by the heated windows, methods provided in embodiments of the invention can be used to derive an appropriate flow-based compensation.

While the oxygen measurement compensation/adjustment techniques described herein can be used in combination with the heater and temperature regulation of the oxygen sensor as set forth above, it is contemplated that the oxygen measurement compensation/adjustment algorithms can be used without temperature regulation of the oxygen sensor, although temperature fluctuations of the temperature sensor would be more dramatic in that instance.

In certain embodiments, methods are provided that can be used to precisely align oxygen and flow signal timing so that accurate oxygen consumption and related metabolic parameters can be accurately estimated. Typically, during the interval 750 between the inspiratory and expiratory phases, flow rate passes briefly through zero. In one embodiment, these corrections are used throughout the breathing cycle; however, the disturbance is most apparent in the uncorrected waveform during rapid changes in flow and/or pressure. This results in a more apparent disturbance in the instantaneous oxygen waveform. The flow-based compensation methods described can reduce or eliminate this disturbance as long as the oxygen and flow signals are temporally aligned. If a misalignment exists, a delay can be introduced to either the flow or oxygen data stream and adjusted until the disturbance is minimized.

It should be appreciated that the present invention can be used in several different gas monitoring applications where it may be desirable to correct the oxygen waveform, such as spirometry, metabolics, oxygen consumption monitoring, FRC estimation, just for example.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system for measuring an amount of a gas component within a gas flow, comprising:
   a gas sensor configured to measure an amount of a component of gas within a flow of gas, wherein the gas sensor has a sensing element configured to contact the flow of gas, and wherein an output of the sensing element is sensitive to temperature fluctuations of the sensing element;
   a pressure sensor configured to measure a pressure of the flow of gas;
   a flow sensor configured to measure the flow of gas; and
   a processor configured to receive first signals as a function of the amount of the component of gas measured by the gas sensor and second signals as a function of the pressure measured by the pressure sensor and the flow measured by the flow sensor, wherein the processor is further configured to adjust the measurement of the amount of the component of gas measured by the gas sensor based upon the measured pressure measured by the pressure sensor and the measured flow measured by the flow sensor, wherein the gas sensor comprises an oxygen sensor, and wherein the processor adjusts the amount of oxygen measured by the oxygen sensor according to the equation:

$$\% \text{oxygen}_{flow\_compensated}[n] = \% \text{oxygen}_{pressure\_compensated}[n] * (1.0 + K_X * \text{flow}_{filtered}[n]),$$

where "% oxygen$_{flow\_compensated}$[n]" is a flow compensated percent oxygen for a current (nth) sample, $K_X = K_I$ during inspiration, $K_X = K_E$ during expiration, "$K_I$" is a compensation factor applied for inspiratory flow, "$K_E$" is a compensation factor applied for expiratory flow, and "flow$_{filtered}$[n]" is a flow signal delayed and low-pass filtered to match a time response of the oxygen signal, and where % oxygen$_{pressure\_compensate}$ [n]=% oxygen$_{raw}$ [n](total airway pressure[n]/barometric pressure) and % oxygen$_{raw}$[n] is a non-pressure compensated oxygen signal measured by the oxygen sensor for the current (nth) sample.

2. The system of claim 1, wherein $K_I$ is between 0.00006 and 0.00018, and $K_E$ is between −0.00020 and −0.00040.

3. The system of claim 1, wherein the sensing element comprises a film coated with a photosensitive chemical.

4. The system of claim 3, wherein the gas sensor further comprises a photodetector that measures radiation emitted by the photosensitive chemical upon exposure to oxygen.

5. The system of claim 1, further comprising a temperature sensor and a thermal regulator to regulate a temperature of the sensing element based on an output of the temperature sensor.

6. The system of claim 1, wherein the processor maintains compensation factors, each of the compensation factors identifying an amount of adjustment of the measurement of the amount of the component of gas corresponding to a measured characteristic associate with the flow of gas.

7. The system of claim 6, wherein the compensation factors are obtained empirically.

8. A system for measuring an amount of oxygen in a gas flow, comprising:
a conduit through which a gas flow passes;
an oxygen sensor having a sensing element exposed to the gas flow within the conduit, the oxygen sensor sensing an amount of oxygen in the gas flow;
a pressure sensor constructed and arranged to measure a pressure of the gas flow in the conduit;
a flow sensor configured to measure a flow rate of the gas flow; and
a processor that receives a first signal based on the amount of oxygen sensed by the oxygen sensor and that receives a second signal based on the pressure measured by the pressure sensor and the flow rate measured by the flow sensor, the processor adjusting the amount of oxygen sensed by the oxygen sensor based on the measured pressure and the measured flow rate,
wherein the processor adjusts the amount of oxygen measured by the oxygen sensor according to the equation:

$$\% \text{oxygen}_{flow\_compensated}[n] = \% \text{oxygen}_{pressure\_compensated}[n] * (1.0 + K_X * \text{flow}_{filtered}[n]),$$

where "% oxygen$_{flow\_compensated}$[n]" is a flow compensated percent oxygen for a current (nth) sample, $K_X = K_I$ during inspiration, $K_X = K_E$ during expiration, "$K_I$" is a compensation factor applied for inspiratory flow, "$K_E$" is a compensation factor applied for expiratory flow, and "flow$_{filtered}$[n]" is a flow signal delayed and low-pass filtered to match a time response of the oxygen signal, and where % oxygen$_{pressure\_compensated}$ [n]=% oxygen$_{raw}$ [n](total airway pressure[n]/barometric pressure) and % oxygen$_{raw}$[n] is a non-pressure compensated oxygen signal measured by the oxygen sensor for the current (nth) sample.

9. The system of claim 8, wherein the sensing element is sensitive to variations in temperature, and wherein the processor adjusts by an adjustment amount the amount of oxygen sensed by the oxygen sensor by an amount calculated to compensate for temperature changes related to the measured pressure and the measured flow rate.

10. The system of claim 9, wherein the adjustment amount is calculated using a compensation factor, the compensation factor identifying the adjustment amount for a plurality of different values of the measured pressure and the measured flow rate.

11. The system of claim 10, wherein the compensation factors are (a) obtained empirically, (b) based on a history of prior measurements provided by the oxygen sensor, (c) provided during calibration of the system, or any combination of (a), (b) and (c).

12. The system of claim 8, further comprising a temperature sensor and a thermal regulator to regulate a temperature of the sensing element based on an output of the temperature sensor.

13. A method of measuring an amount of oxygen in a flow of gas, comprising the acts of:
measuring an amount of oxygen in a gas flow;
measuring a characteristic associated with the gas flow; and
adjusting by a processor the measurement of the amount of oxygen in the gas flow based upon the measured characteristic associated with the gas flow and according to the equation:

$$\% \text{oxygen}_{flow\_compensated}[n] = \% \text{oxygen}_{pressure\_compensated}[n] * (1.0 + K_X * \text{flow}_{filtered}[n]),$$

where "% oxygen$_{flow\_compensated}$[n]" is a flow compensated percent oxygen for a current (nth) sample, $K_X = K_I$ during inspiration, $K_X = K_E$ during expiration, "$K_I$" is a compensation factor applied for inspiratory flow, "$K_E$" is a compensation factor applied for expiratory flow, and "flow$_{filtered}$[n]" is a flow signal delayed and low-pass filtered to match a time response of the oxygen signal, and where % oxygen$_{pressure\_compensated}$ [n]=% oxygen$_{raw}$ [n](total airway pressure[n]/barometric pressure) and % oxygen$_{raw}$[n] is a non-pressure compensated oxygen signal measured by the oxygen sensor for the current (nth) sample.

14. The method of claim 13, wherein the act of adjusting includes the acts of:
determining a compensation factor based on an instantaneous measurement of the measured characteristic, and
modifying the measurement of the amount of oxygen based on the compensation factor.

15. The method of claim 14, wherein the act of modifying includes (a) scaling the measurement of the amount of oxygen using the compensation factor, (b) adding the compensation factor to the measurement of the amount of oxygen, or both (a) and (b).

16. The method of claim 14, wherein the compensation factors are obtained empirically.

17. The method of claim 13, wherein the characteristic is a flow rate measured by a flow sensor, or a pressure measured by a pressure sensor.

18. The method of claim 13, wherein the amount of oxygen is measured by a sensing element comprising a film coated with a photosensitive chemical.

19. The method of claim 18, wherein the sensing element further comprises a photodetector that measures radiation emitted by the photosensitive chemical upon exposure to oxygen.

20. The method of claim 18, further comprising the acts of:
measuring a temperature indicative of a temperature of the sensing element; and
controlling the temperature of the sensing element based on the measured temperature.

21. A system for measuring an amount of a gas component within a gas flow, comprising:
means for measuring an amount of a component of gas within a gas flow;
means for measuring a characteristic associated with the gas flow, wherein the measured characteristic includes a pressure of the gas flow and a flow rate of the gas flow; and
means for adjusting the measured amount of the component of gas based upon the measured characteristic associated with the gas flow,
wherein the gas comprises oxygen, and wherein the means for adjusting adjusts the amount of oxygen measured by the means for measuring according to the equation:

$$\%\ \text{oxygen}_{flow-compensated}[n] = \%\ \text{oxygen}_{pressure-compensated}[n]*(1.0 + K_X*\text{flow}_{filtered}[n]),$$

where "% oxygen$_{flow-compensated}$[n]" is a flow compensated percent oxygen for a current (nth) sample, $K_X = K_I$ during inspiration, $K_X = K_E$ during expiration, "$K_I$" is a compensation factor applied for inspiratory flow, "$K_E$" is a compensation factor applied for expiratory flow, and "flow$_{filtered}$[n]" is a flow signal delayed and low-pass filtered to match a time response of the oxygen signal, and where % oxygen$_{pressure-compensated}$[n]=% oxygen$_{raw}$[n](total airway pressure[n]/barometric pressure) and % oxygen$_{raw}$[n] is a non-pressure compensated oxygen signal measured by the oxygen sensor for the current (nth) sample.

22. The system of claim 21, wherein the means for measuring an amount of a component of gas includes means for measuring radiation emitted by a photosensitive element, and wherein the radiation is emitted responsive to exposure of the photosensitive element to oxygen.

23. The system of claim 22, further comprising means for regulating a temperature of the photosensitive element.

24. The system of claim 21, wherein the amount of oxygen is measured as a partial pressure of oxygen within the gas flow.

25. The system of claim 21, wherein the means for adjusting the measured amount includes means for identifying a compensation factor for calculating an amount of adjustment of the measurement of the amount of the component of gas corresponding to the measured characteristic.

26. The system of claim 1, wherein the processor is further configured to temporally align the first signals and the second signals.

27. The system of claim 8, wherein the processor is further configured to temporally align the first signal and the second signal.

28. The method of claim 13, wherein the measured characteristic includes pressure measured by a pressure sensor and a flow measured by a flow sensor.

29. The method of claim 13, wherein the measured characteristic associated with the gas flow comprises a measured flow rate of the gas flow, the method further comprising the act of temporally aligning a first signal representing the measured amount of oxygen and a second signal representing the measured flow rate of the gas flow.

30. The system of claim 21, further comprising means for temporally aligning a first signal representing the measured amount of the component of the gas and a second signal representing the measured flow rate.

* * * * *